(12) United States Patent
Hilton, Jr.

(10) Patent No.: US 7,838,719 B2
(45) Date of Patent: Nov. 23, 2010

(54) BANDAGE FOR COVERING A WOUND WITH NO ADHESIVE-TO-SKIN CONTACT

(76) Inventor: Jimmy Earl Hilton, Jr., P.O. Box 1040, Hudson, NC (US) 28638

( * ) Notice: Subject to any disclaimer, the term of this patent is extended or adjusted under 35 U.S.C. 154(b) by 386 days.

(21) Appl. No.: 11/338,408

(22) Filed: Jan. 24, 2006

(65) Prior Publication Data

US 2007/0078367 A1     Apr. 5, 2007

Related U.S. Application Data

(60) Provisional application No. 60/722,702, filed on Oct. 3, 2005.

(51) Int. Cl.
*A61F 13/00*     (2006.01)
(52) U.S. Cl. ............... 602/58; 602/41; 602/42; 602/53; 602/60; 602/75
(58) Field of Classification Search ............. 602/60–65, 602/41–59, 75–77; 604/352; 424/443, 445, 424/447, 448; 128/106.1, 107.1, 112.1, 114.1, 128/116.1
See application file for complete search history.

(56) References Cited

U.S. PATENT DOCUMENTS

| | | | |
|---|---|---|---|
| 2,477,403 A * | 7/1949 | Brady .................... 602/43 |
| 3,973,563 A | 8/1976 | Green et al. | |
| 4,034,751 A * | 7/1977 | Hung ..................... 602/52 |
| 4,666,441 A * | 5/1987 | Andriola et al. ......... 424/448 |
| 4,822,617 A * | 4/1989 | Panoz .................... 424/449 |
| 5,456,660 A * | 10/1995 | Reich et al. ............ 602/79 |
| 5,607,388 A * | 3/1997 | Ewall .................... 602/58 |
| 5,674,523 A * | 10/1997 | Cartmell et al. ......... 424/445 |
| 5,683,354 A | 11/1997 | Levy | |
| 5,939,339 A * | 8/1999 | Delmore et al. ......... 442/149 |
| 5,947,917 A | 9/1999 | Carte et al. | |
| 5,962,011 A * | 10/1999 | DeVillez et al. ......... 424/448 |
| 6,255,552 B1 * | 7/2001 | Cummings et al. ....... 602/58 |
| 6,307,118 B1 * | 10/2001 | Reich .................... 602/42 |
| 6,700,032 B1 * | 3/2004 | Gray ..................... 602/48 |
| 2004/0015115 A1 * | 1/2004 | Sinyagin ................ 602/42 |

* cited by examiner

*Primary Examiner*—Nicholas D Lucchesi
*Assistant Examiner*—Keri J Nicholson

(57) ABSTRACT

The invention relates to a self-adhering bandage that is secured in place without an adhesive/skin contact point. The bandage may include a substance storage area that houses a substance that is transferred to the dressing component when pressure is applied to the substance storage area.

19 Claims, 18 Drawing Sheets

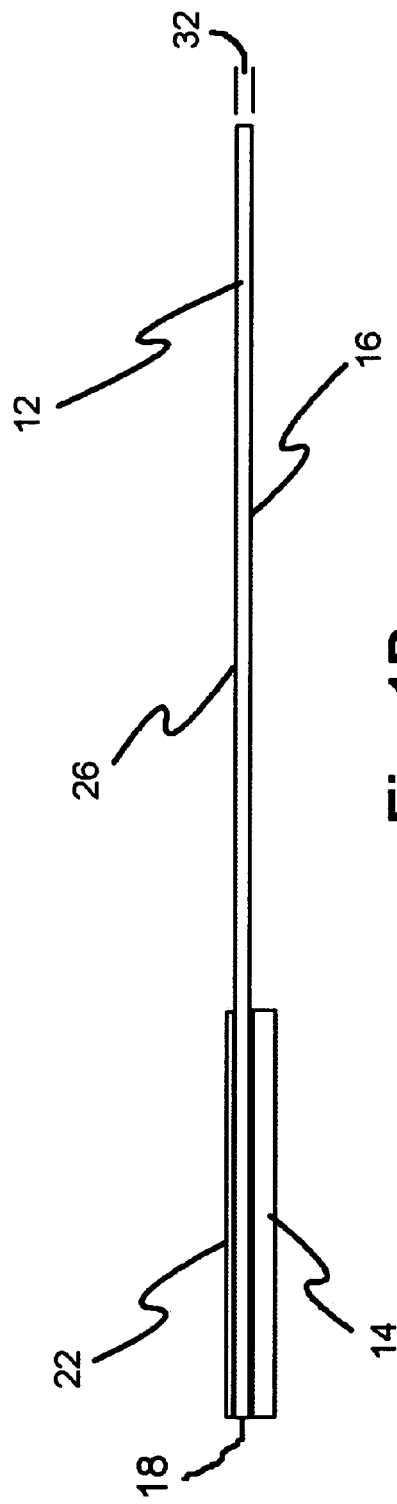
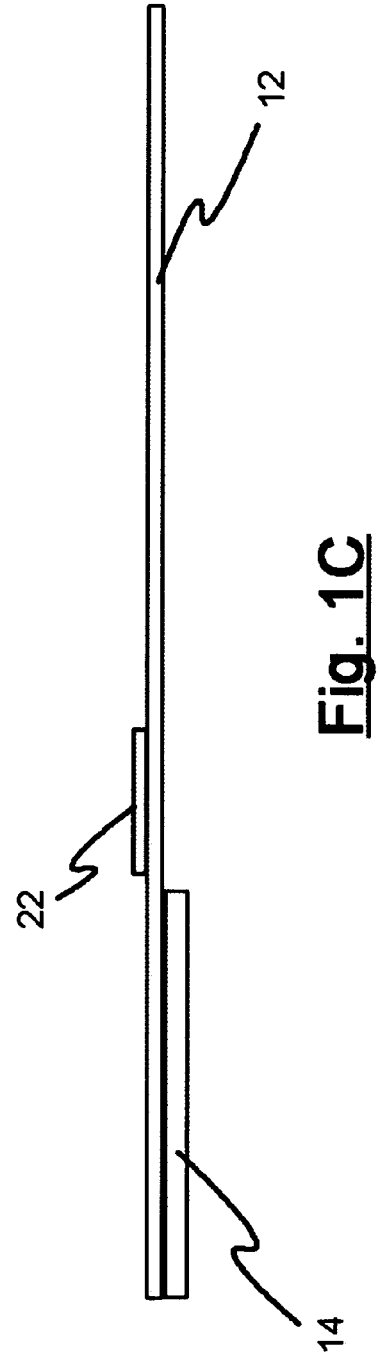

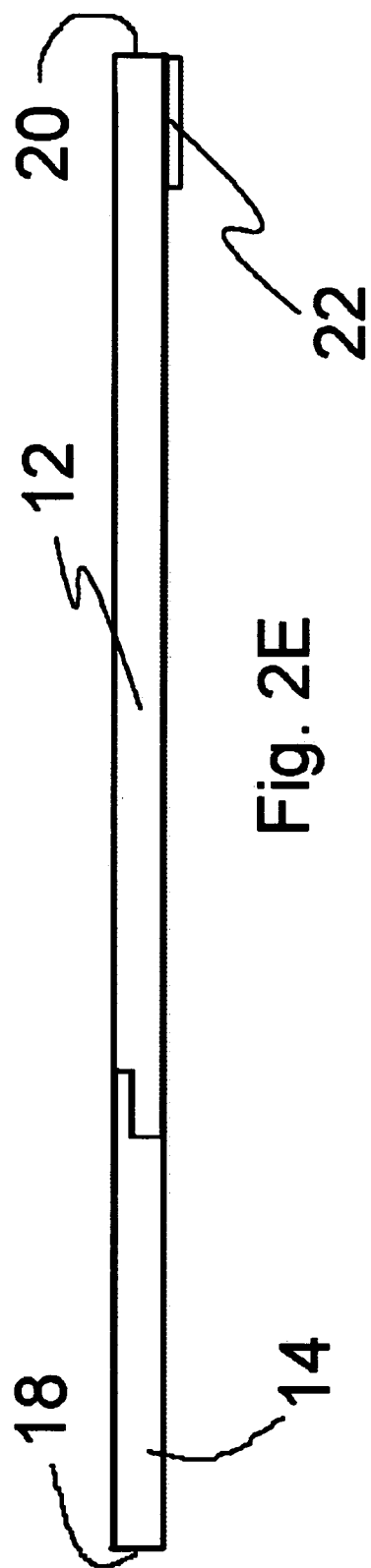
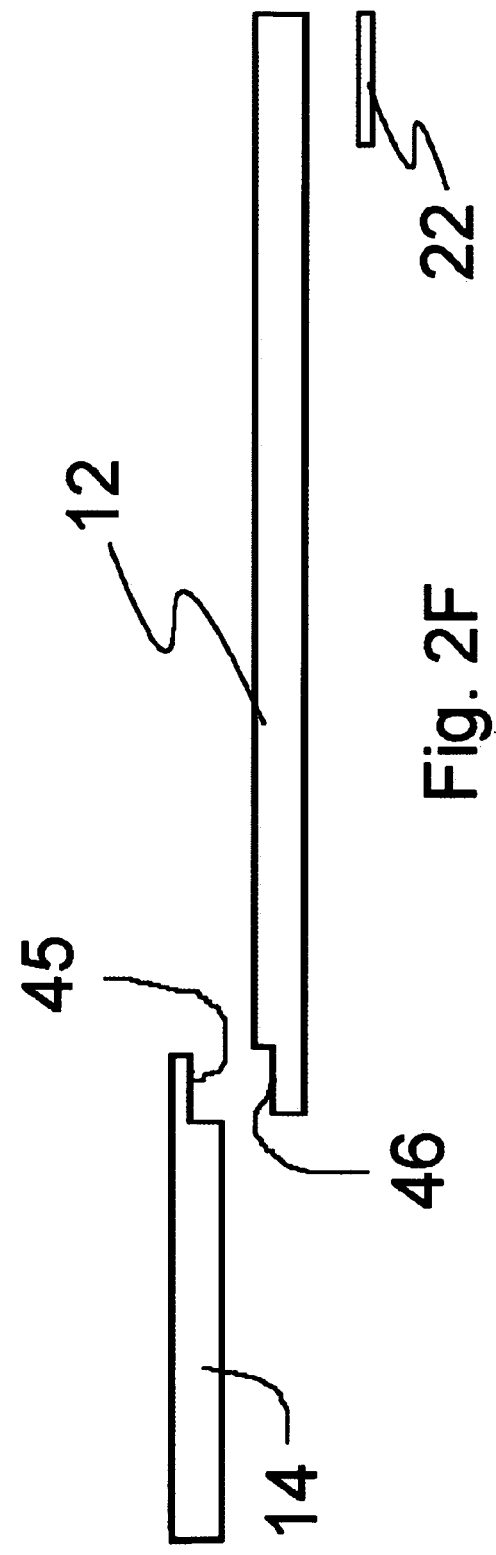
Fig. 2E
Fig. 2F

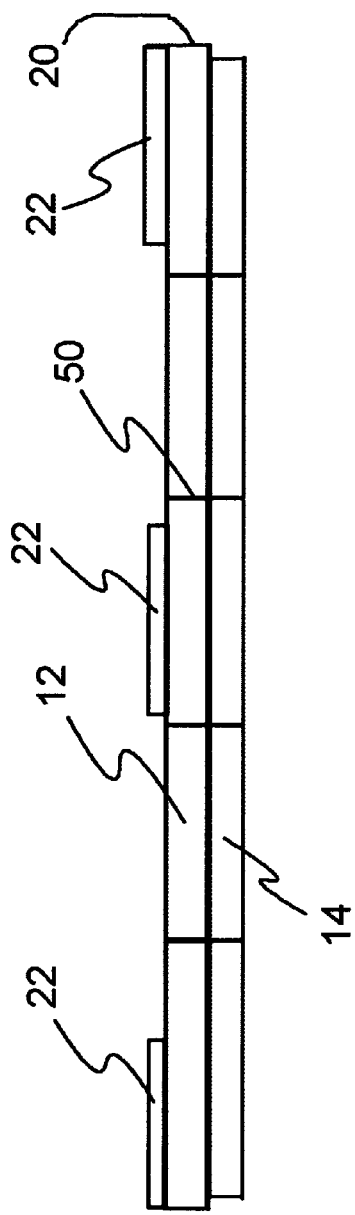
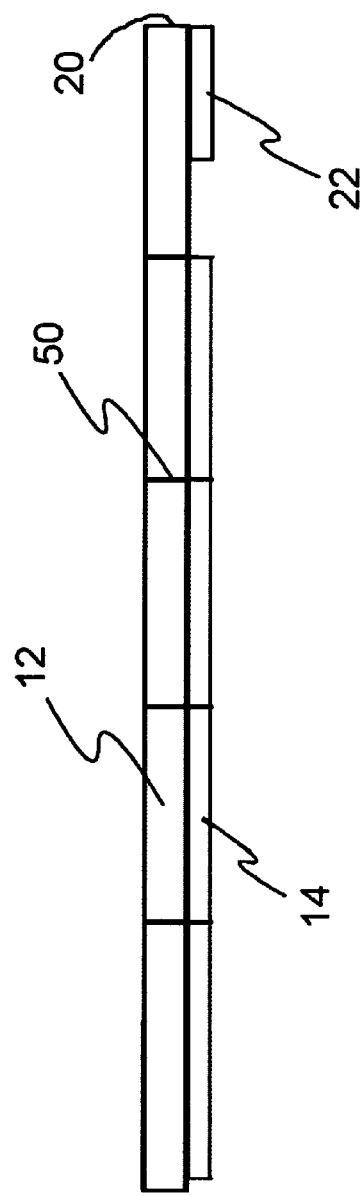
Fig. 4B
Fig. 4C

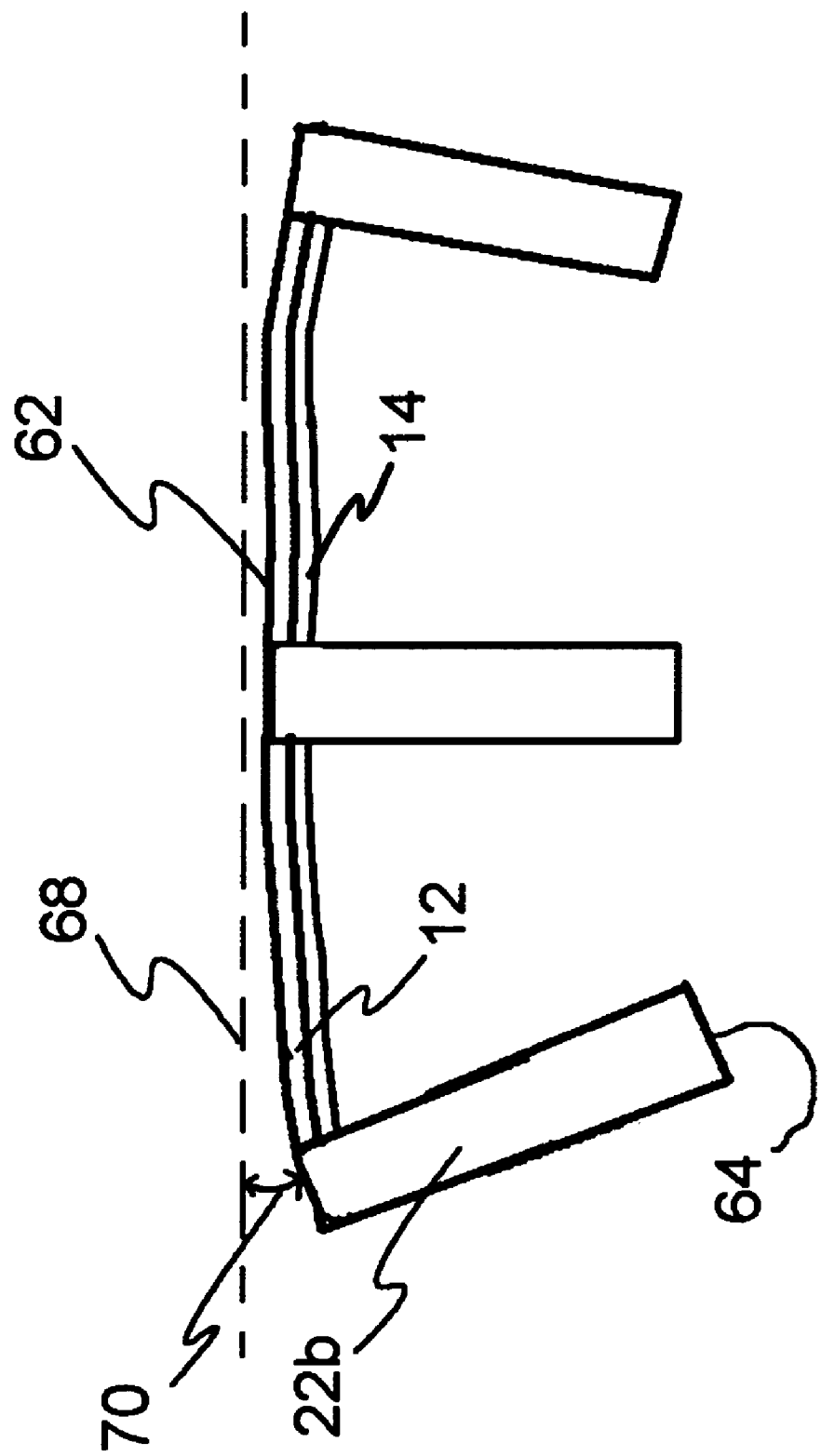

BANDAGE FOR COVERING A WOUND WITH NO ADHESIVE-TO-SKIN CONTACT

CLAIM TO PRIORITY

This application claims priority from U.S. Provisional Patent Application No. 60/722,702, filed Oct. 3, 2005, the entire contents of which are incorporated herein by reference.

TECHNICAL FIELD OF THE INVENTION

The present invention relates to a bandage for covering a wound. One embodiment of the bandage comprises a non-stick pad section positioned at one end of a first side of the bandage for covering a wound. The bandage further comprises an adhering section disposed on the second side of the bandage substantially adjacent to the pad section. The adhering section is configured for attaching to the bandage instead of the patient thereby providing a bandage that does not include adhesives intended to that stick to a patient's skin.

BACKGROUND OF TH INVENTION

A wide variety of products are currently available in the medical field for use as bandages in treating surgical incisions, abrasions, cuts, burns, and other various wounds. Plain and medicated bandages are widely employed in a variety of environments including hospitals (after major surgery) and private homes (for minor accidental injuries). Such bandages are used on various parts of the body to protect wounds from contamination and from further injury. However, in spite of their wide acceptance, such prior art bandages are not without their disadvantages.

Prior art bandages, such as Band-Aids® for example, usually comprise a backing, a cushion or pad, and typically two or more pressure sensitive adhesive masses coated on portions of one side of the backing for attaching the bandage to the patient's skin. Since such bandages include an adhesive/skin contact point, it was necessary to formulate adhesives which provide adherence of the bandage to the skin while still exhibiting the necessary degree of release when intentionally removing the bandage so as not to damage the skin. For many types of wounds, frequent changes of such bandages are necessary to observe the healing process and to apply medications. Unfortunately, frequent removal of the adhesive section from contact with the skin will eventually cause trauma to even relatively healthy skin and is particularly undesirable for patients with poor circulation, something common among older patients with diabetes.

Additionally, it is known that during an active day for a typical person, portions of the human skin stretch as much as 30% of its outstretched size. Such stretching typically shortens the adhesive life of an adhesive bandage and often results in objectionable transfer of adhesive from the bandage to the skin. Thus, for such bandages, it is desirable for the adhesive layer to have a flexible quality characteristic of rubber based adhesives. Unfortunately, rubber based adhesives may irritate the wound or the surrounding healthy skin. Restated, adhesives used by an adhesive-to-skin contact bandage should be hypoallergenic, which is not a characteristic of natural rubber based adhesives.

What is needed is a bandage that will reduce or eliminate the above described disadvantages by not requiring an adhesive-skin contact point thereby allowing any type of adhesive to be used.

Another problem with prior art bandages concerns issues relating to efficiency and versatility. No single dressing is suitable for all types of wounds. Different types of wounds and the different stages of healing typically require different dressings or combinations of dressings. Indeed, a number of different types of dressings may be used during the healing process of a single wound. Notably, however, the wound site does not change, and thus, the bandage configuration/size that attaches to the body best should not change significantly over short durations of time. Once an optimal bandage shape/configuration is established for a particular wound site, especially for larger wounds, it would be convenient and more efficient to use the same bandage shape and only change the dressing or pad.

As noted above, prior art bandages usually comprise a backing, a cushion or pad, and typically two or more pressure sensitive adhesive masses coated on portions of one side of the backing for attaching the bandage to the patient's skin. Since such bandages include an adhesive/skin contact point, the entire bandage is typically discarded after a single use. What is needed is a bandage that comprises a replaceable/configurable pad section that allows the non-pad section to be reused.

SUMMARY

Some of the objects and advantages of the invention will now be set forth in the following description, while other objects and advantages of the invention may be obvious from the description, or may be learned through practice of the invention.

Broadly speaking, a principle object of the present invention is to provide a self-adhering bandage that is secured in place without an adhesive/skin contact point.

Another general object of the present invention is to provide a configurable self-adhering bandage that can be configured with one or more dressing components for covering a wound.

Still another general object of the present invention is to provide a bandage that comprises a substance storage area that houses a substance that is transferred to the dressing component when pressure is applied to the substance storage area.

A still further general object of the present invention is to provide for a sectional self-adhering bandage that is perforated so that the sections of the bandage can be removed as needed to better fit the size of a wound.

Additional objects and advantages of the present invention are set forth in the detailed description herein or will be apparent to those skilled in the art upon reviewing the detailed description. Also, it should be further appreciated that modifications and variations to the specifically illustrated, referenced, and discussed steps, or features hereof may be practiced in various uses and embodiments of this invention without departing from the spirit and scope thereof, by virtue of the present reference thereto. Such variations may include, but are not limited to, substitution of equivalent steps, referenced or discussed, and the functional, operational, or positional reversal of various features, steps, parts, or the like. Still further, it is to be understood that different embodiments, as well as different presently preferred embodiments, of this invention may include various combinations or configurations of presently disclosed features or elements, or their equivalents (including combinations of features or parts or configurations thereof not expressly shown in the figures or stated in the detailed description).

One exemplary embodiment of the present invention relates to novel implementations of self-adhering bandaging technology for covering a wound. For such an exemplary embodiment, the bandage comprises a backing component of a predetermined b-thickness, b-length, and b-width. The backing component defines a first face opposed by a second face as well as a first end and a second end. The bandage further comprises a dressing component associated with said first face at the first end of said backing component. An attachment mechanism is associated with at least one of the second face at the first end of said backing component and the first face of said backing component. The bandage is of sufficient size to allow the dressing component to cover the wound and the backing component to wrap around the body part comprising the wound so that the attachment mechanism attaches the backing component to itself thereby securing the bandage in place without the need for an adhesive/skin contact point. Preferably, at least part of the backing material is composed of a material that does not easily slide across skin.

The bandage may further comprise a dressing component receiver attached to the backing component. The dressing component receiver is configured for releasably receiving at least one of a plurality of different dressing components. Alternatively, the dressing component may be attached directly to the backing component for embodiments where the dressing component receiver is integral to the backing component.

The dressing component is appropriately configured for providing the best healing environment for a wound. For one embodiment, the dressing component is configured to keep the wound bed moist with exudates. For example, the dressing component may comprise any one of a (a) antimicrobial dressing, (b) diabetic gel dressing, and (c) cutinova dressing. Additionally, the dressing component may be composed of transparent material that allows viewing of the wound without removing the bandage. A patch constructed from materials in the fluoropolymers family and coated with a moisturizing layer may also be used for applications covering large areas.

It is well known that different types of wounds and the same wound at different stages of healing require different dressings or combinations of dressings. Consequently, the dressing component may comprise a plurality of sections having different properties for covering two different wounds within close proximity of each other or for covering one wound that has wound sections at different states of healing. Such a dressing component may comprise any number of sections comprising one ore more of a passive section, an interactive section, and a bioactive section.

Additionally, the backing component may be configured to define a void between the first face and the second face. The void is configured for housing substances including moisturizing creams, an antibiotic creams, and medications. The dressing component is associated with the void via a passage between the dressing component and the void. When pressure is applied to the void, at least part of the substance is transferred from the void to the dressing component. The passage between the dressing component and the void may be a one way passage.

A still further embodiment of the invention concerns a self-adhering bandaging technology for covering a wound comprising a backing component of a predetermined b-thickness, b-length, and b-width. The backing component defines a first face opposed by a second face and a first end and a second end. The bandage further comprises a dressing receiver configured for receiving a dressing component and wherein the dressing receiver is one of (a) integral to the backing component, and (b) associated with said backing component. The dressing receiver is associated with the first face at the first end of the backing component. A dressing component is associated with the dressing receiver.

The backing component is either comprised of a material that adheres to itself or is associated with an attachment mechanism on one of the backing component faces. The bandage is of sufficient size to allow (1) the dressing component to cover the wound, and (2) the backing component to wrap around the body part comprising the wound so that the backing component attaches to itself thereby securing the bandage in place.

As before, the dressing component may comprise a plurality of sections having different properties. For example, the dressing component may comprise at least two sections selected from the group of sections consisting of (a) passive section, (b) interactive section, and (c) bioactive section. Additionally, the bandage may comprise a plurality of dressing receivers configured for receiving a dressing component.

Another exemplary embodiment of the present invention concerns methodology for making a self-adhering bandage. The first step in the preferred method is to form a backing component having a predetermined b-thickness, b-length, and b-width. The backing component has a first face opposed by a second face and defines a first end and a second end. The next step in the method is to associate or attach a dressing component to the backing component. For one preferred method, the dressing component is attached to the first face of the backing component at the first end of the backing component. The next step in the method is to provide an attachment mechanism for attaching the backing component to itself thereby securing the bandage in pace when positioned over a wound. The attachment mechanism is either an inherent property of the material that makes up the backing component (e.g. the material sticks to itself and substantially nothing else) or it is a mechanism disposed on a face of said backing component.

The method may further comprise the step of providing a substance storage area disposed between said first face and said second face wherein said substance is transferred to the dressing component when pressure is placed on said substance storage area. The substance may be any number of substances such as antibiotic ointment, moisturizing creams, and medications.

The method may further comprise providing a dressing component comprising a plurality of sections having different properties such as a passive dressing, interactive dressing and polymeric dressing. Different types of wounds and the different stages of a healing wound typically require different dressings or combinations of dressings. In this step, the two different dressing components (having different healing properties) are strategically disposed along the backing component for covering two different wounds or different sections of the same wound.

Those of ordinary skill in the art will better appreciate the features and aspects of such embodiments, and others, upon review of the remainder of the specification.

BRIEF DESCRIPTION OF THE DRAWINGS

A full and enabling description of the present subject matter, including the best mode thereof, directed to one of ordinary skill in the art, is set forth in the specification, which makes reference to the appended figures, in which:

FIG. 1B is a side plane view of the self-adhering bandage depicted in FIG. 1;

FIG. 1C is a side plane view of the self-adhering bandage depicted in FIG. 1 with the attachment mechanism in a different location;

FIG. 2E depicts an alternative embodiment of a dressing component receiver;

FIG. 2F depicts a side exploded view of the bandage shown in FIG. 2E;

FIG. 4B is a side plane view of the self-adhering bandage depicted in FIG. 4 with additional attachment mechanism sections;

FIG. 4C is a side plane view of an alternative embodiment of the bandage depicted in FIG. 4B;

FIG. 5C is a side plane view of the self-adhering bandage depicted in FIG. 5A and FIG. 5B;

Figure 1:
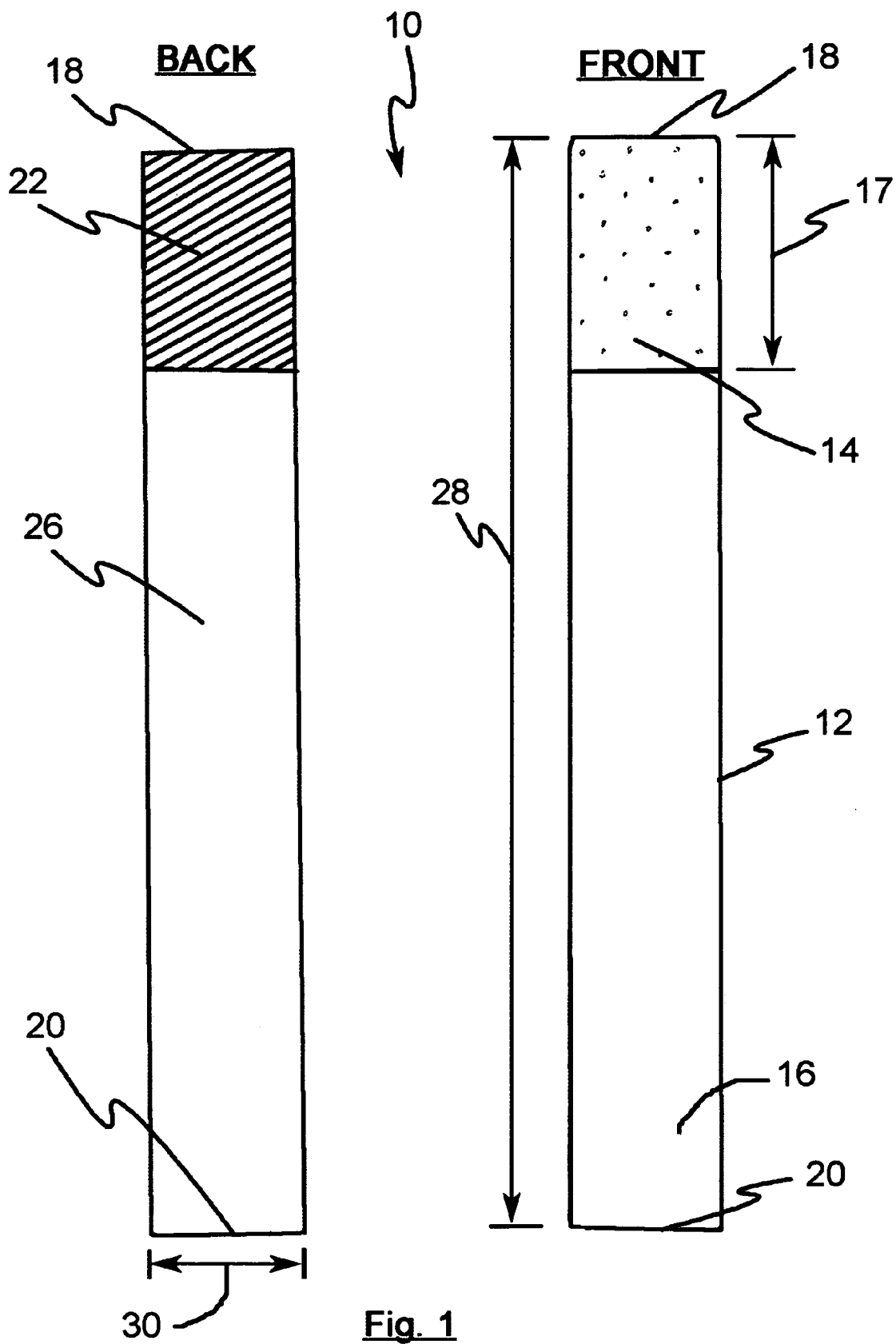
FIG. 1 depicts a back view and a front view of a self-adhering bandage according to one embodiment of the present invention.

Repeat use of reference characters throughout the present specification and appended drawings is intended to represent the same or analogous features or elements of the present technology.

DETAILED DESCRIPTION

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used on another embodiment to yield a still further embodiment. Thus, it is intended that the present invention covers such modifications and variations as come within the scope of the appended claims and their equivalents. Other objects, features, and aspects of the present invention are disclosed in or may be determined from the following detailed description. Repeat use of reference characters is intended to represent same or analogous features, elements or steps. It is to be understood by one of ordinary skill in the art that the present discussion is a description of exemplary embodiments only, and is not intended as limiting the broader aspects of the present invention.

While the particulars of the present invention and associated technology may be adapted (size, shape, materials) for use with many different parts of the body to cover a wide variety of wounds, the examples discussed herein are particularly directed to applications where an adhesive/skin contact point is not desirable.

Referring now to FIG. 1, a front/back view of a self-adhering bandage (10) according to one embodiment of the present invention is depicted. For the embodiment depicted in FIG. 1, bandage (10) is composed of a backing component (12) that runs the full length of the bandage. Backing component (12) has a predetermined b-length (28), b-width (30), and b-thickness (32, FIG. 1B). Backing component (12) defines a first end (18) and a second end (20) as well as a first face (16) and an opposing second face (26). As depicted in FIG. 1B, first face (16) and second face (26) are substantially parallel to each other when first end (18) is in alignment with second end (20) as shown in FIG. 1 and FIG. 1B.

A dressing component (14) is associated with backing component (12). For the embodiment shown in FIG. 1, dressing component (14) is located at the first end (18) and extends a predefined distance (17) along the backing component. For this embodiment of the invention, the width of the dressing component is substantially equal to b-width (30) and the thickness of the dressing component is substantially equal to b-thickness (32).

Referring now to FIG. 1B, an attachment mechanism (22) is shown associated with the second face (26) of backing component (12) at the first end (18). Such a configuration positions the attachment mechanism (22) adjacent to dressing component (14) with backing component (12) separating the two items. It will be appreciated that attachment mechanism (22) may be positioned at any point along backing component (12) with the only constraints being those described latter in this document. For example, FIG. 1C depicts one possible alternative embodiment where attachment mechanism (22) is positioned between first end (18) and second end (20) and not adjacent to dressing component (14). Attachment mechanism (22) may run the full length of backing component (12) for some embodiments of the invention.

Figure 1D:
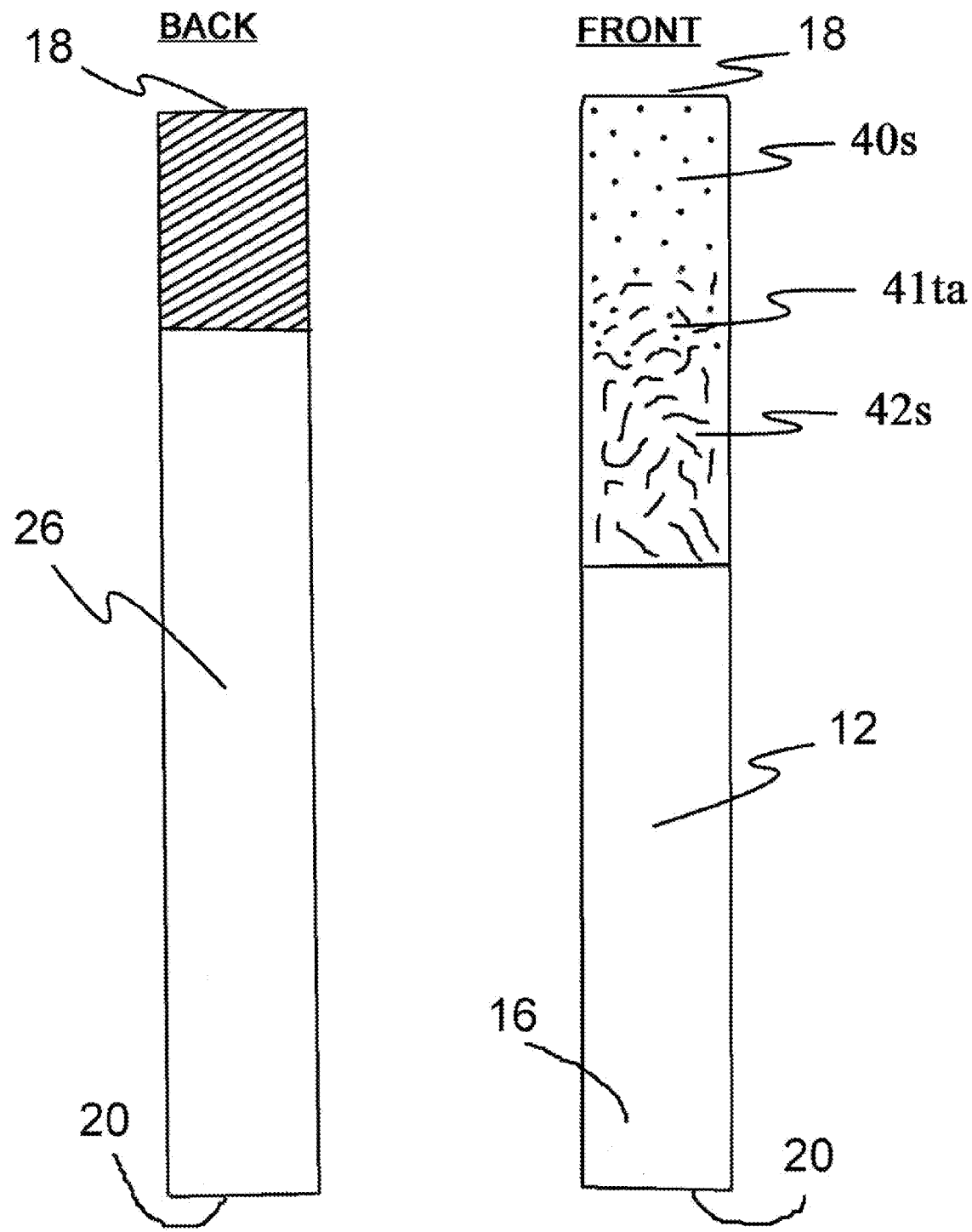
FIG. 1D is a back view and a front view of a self-adhering bandage according to an alternative embodiment of the present invention comprising a dressing component with two different sections.
Figure 1E:
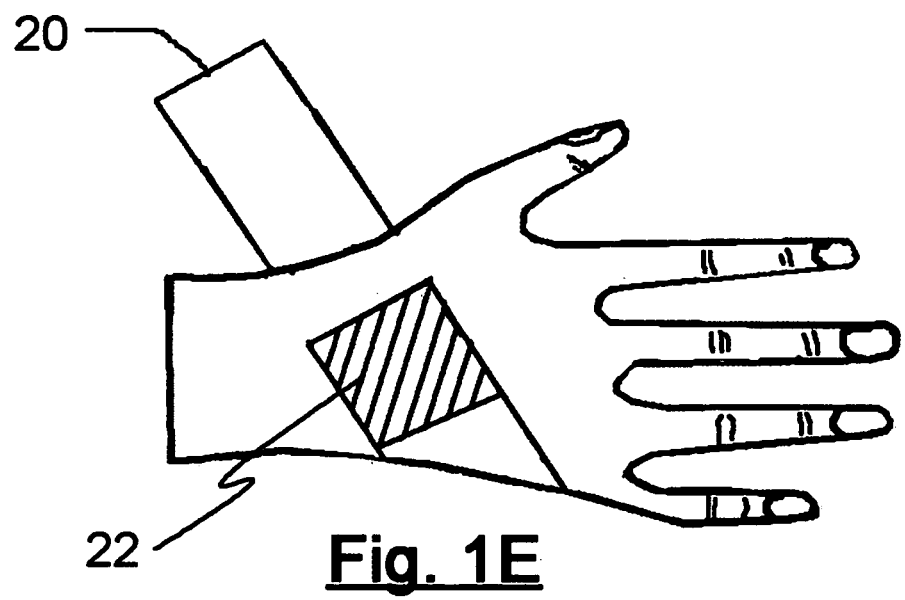
FIG. 1E is a top perspective view of a self-adhering bandage being applied to the back of a hand.
Figure 1F:
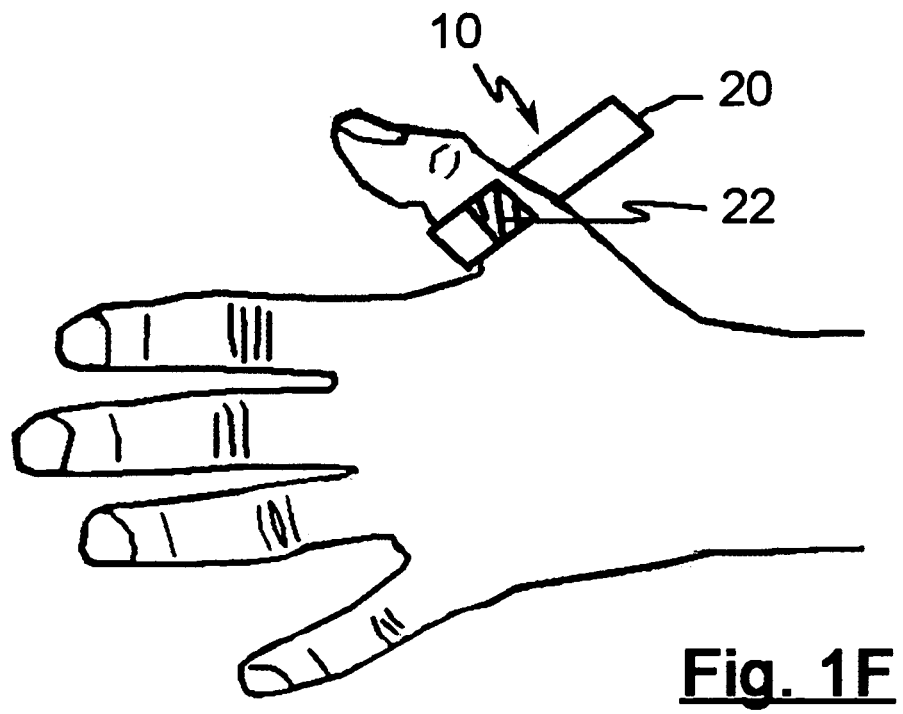
FIG. 1F is a top perspective view of a self-adhering bandage being applied to a thumb.

As shown if FIG. 1E and FIG. 1F, bandage (10) may be configured to have any number of predefined shape and sizes. The size of bandage (10) for FIG. 1E is wider and longer than the size of the bandage (10) in FIG. 1F. Both bandages, however, are of sufficient size to allow (1) the dressing component to cover the wound being treated, and (2) the backing component to wrap around the body part comprising the wound so that the attachment mechanism (22) attaches the backing component to itself thereby securing the bandage in place without a adhesive/skin contact point. Thus, for this embodiment of the invention, it should be appreciated that attachment mechanism (22) may be positioned at any location along second face (26) as long as second end (20) can reach attachment mechanism (22) when the bandage (10) is applied to a wound as shown in FIG. 1E and FIG. 1F.

Attachment mechanism (22) may be constructed from any number of suitable technologies. For one embodiment of the invention, attachment mechanism (22) may be an inherent property of backing component (12). For example, backing component (12) may be a self-adherent elastic wrap that sticks to itself without adhesive. Coban is one example of such a warp. Other possible embodiments for attachment mechanism (22) include an adhesive layer and/or a hook and loop configuration.

Similarly, backing component (12) may be constructed from any number of suitable technologies for securing the selected dressing component (14) in place over a wound. For example, a rubber elastic material may be used that provides consistent support and mild compression for sprains and strains while also securing a dressing over a wound in the same general area. Such technologies are well known and understood by those skilled in the art, and a detailed explanation thereof is not necessary for purposes of describing the method and system according to the present invention.

The various configurations for dressing component (14) are now considered. It should be appreciated that different types of wounds and the different stages of a healing for a particular wound will typically require different dressings or combinations of dressings. The dressing component (14) may be comprised of any number of dressing technologies and is preferably selected to specifically address the wound to be covered and would typically provide one more of the following: maintain a moist environment at the wound/dressing interface, absorb excess exudate without leakage to the surface of the dressing, provide thermal insulation and mechanical protection, provide bacterial protection, allow gaseous and fluid exchange, absorb wound odor, be non-adherent to the wound and easily removed without trauma, provide some debridement action (remove dead tissue and/or foreign particles), and be non-toxic, non-allergenic and non-sensitizing (to both patient and medical staff).

Dressing component (14) may be a polyurethane based dressing specifically designed to provide a moist wound environment. The basic concept behind moist wound healing is that the presence of exudate in a wound will provide an environment that stimulates healing. Cutinova dressings are one example of dressings which may be designed to provide a moist healing environment for different types of wounds at every stage of severity. Dressing (14) may further comprise a broad-spectrum antimicrobial agent combined with substances for bacterial toxin management and odor control. Examples of such a dressing include the ACTISORB Silver 220 dressings. Alternatively, dressing component (14) may comprise a patch constructed from materials in the fluoropolymers family and coated with a moisturizing layer to prevent the dressing from sticking to a wound. Such a bandage may be particularly useful in bandaging large areas.

Dressing component (14) may comprise a thin layer of absorbent cotton fibers, enclosed in a sleeve of poly(ethylene terephthalate) that is perforated in a regular pattern and sealed along two edges. The plastic film is present to prevent the dressing adhering to the surface of the wound, and is perforated to allow the passage of exudate from the wound into the body of the pad. One example of such dressings is the TELFA pad.

For other embodiments, dressing component (14), backing component (12) and attachment mechanism (22) (depending on attachment mechanism (22) location) may be composed of transparent material configured to allow viewing of the wound without removing the bandage. Transparent dressings are typically made of a thin, transparent polyurethane film. Wound care applications for such dressings include incisions, pressure ulcers, skin biopsies, donor sites, second-degree burns and surgical incisions. Hydrogel is one example of a transparent dressing made of 30% water in an absorbent gel matrix, bonded to a moisture/vapor-permeable barrier film.

As previously noted, dressing component (14) may comprise a plurality of sections where each section is configured for addressing different types of wounds and the different stages of healing for a particular wound. Restated, dressing component (14) may comprise a plurality of sections having different properties such as (a) a passive section, (b) an interactive section, and (c) a bioactive section.

Examples of dressings comprising a passive section include traditional dressings that provide cover over the wound such as gauze and tulle dressings. Such dressings can stick to a wound surface and disrupt the wound bed when removed and are typically only used on minor wounds or as secondary dressings.

Examples of dressings comprising an interactive section include polymeric films and forms which are mostly transparent, permeable to water vapor and oxygen, non-permeable to bacteria (e.g. hyaluronic acid, hydrogels, and foam dressings).

Examples of dressings comprising a bioactive section include dressings which deliver substances active in wound healing such as hydrocolloids, alginates, collagens, and chitosan. Hydrocolloids, for example, are composed mainly of cellulose that turns into a gel when exudate is absorbed. This creates a warm, moist environment that promotes debridement and healing. Depending on the hydrocolloid dressing chosen, such a dressing is suitable for wounds with light to heavy exudate, sloughing or granulating wounds.

Referring now to FIG. 1D, dressing (14) may comprise a plurality of sections where each section is configured for addressing different types of wounds and the different stages of healing for a particular wound. For the dressing shown in FIG. 1D, dressing component (14) comprises dressing section (40s), dressing section (42s), and a transition area (41ta). It will be appreciated that dressing component (14) configurations that do not include a transition area fall within the intended scope of the present invention. For the dressing component configuration shown in FIG. 1D, dressing section (40s) may be, for example, a passive section whereas dressing section (42s) may be an interactive section.

Figure 2:
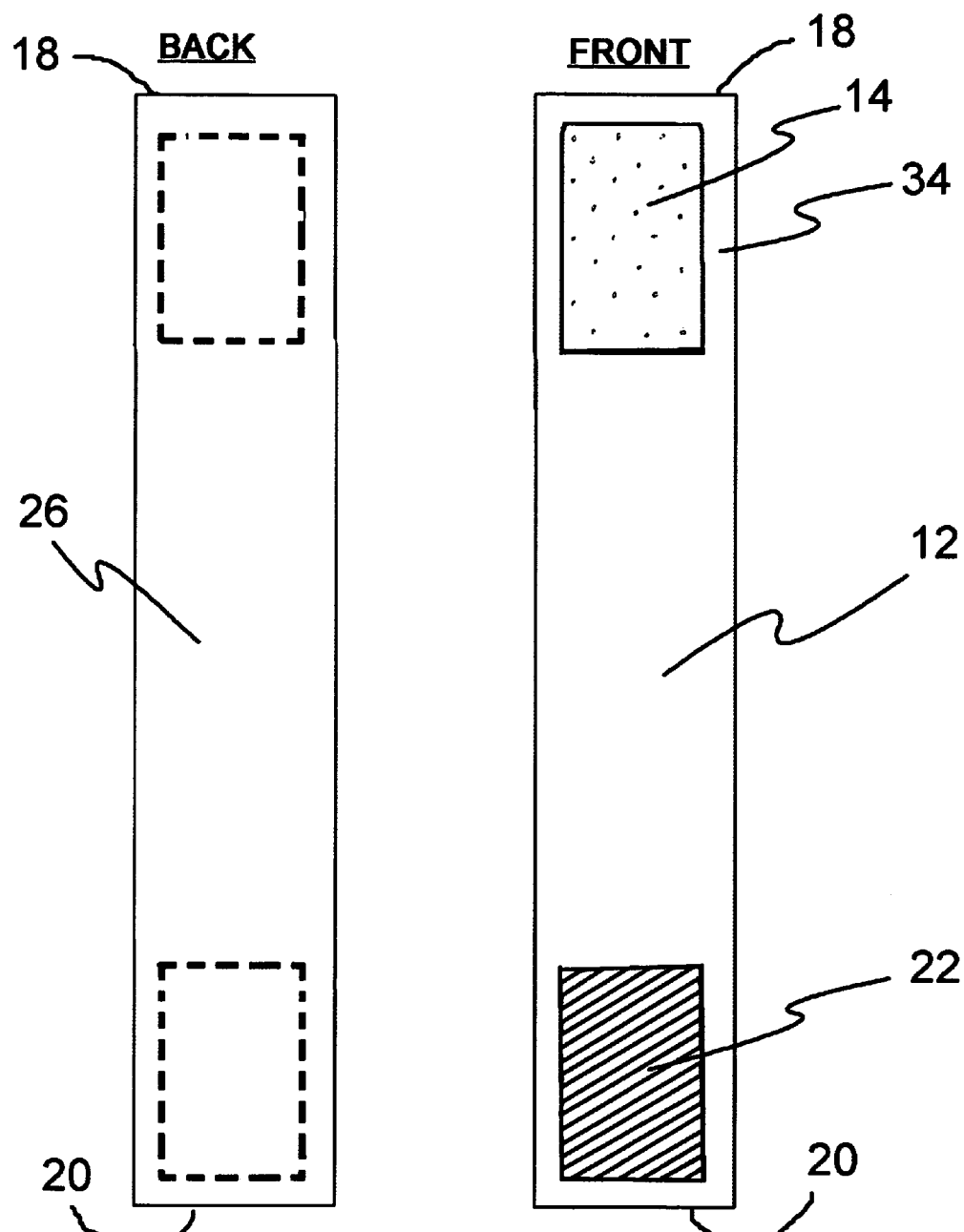
FIG. 2 is a back view and a front view of a self-adhering bandage according to another alternative embodiment of the present invention.
Figure 2B:
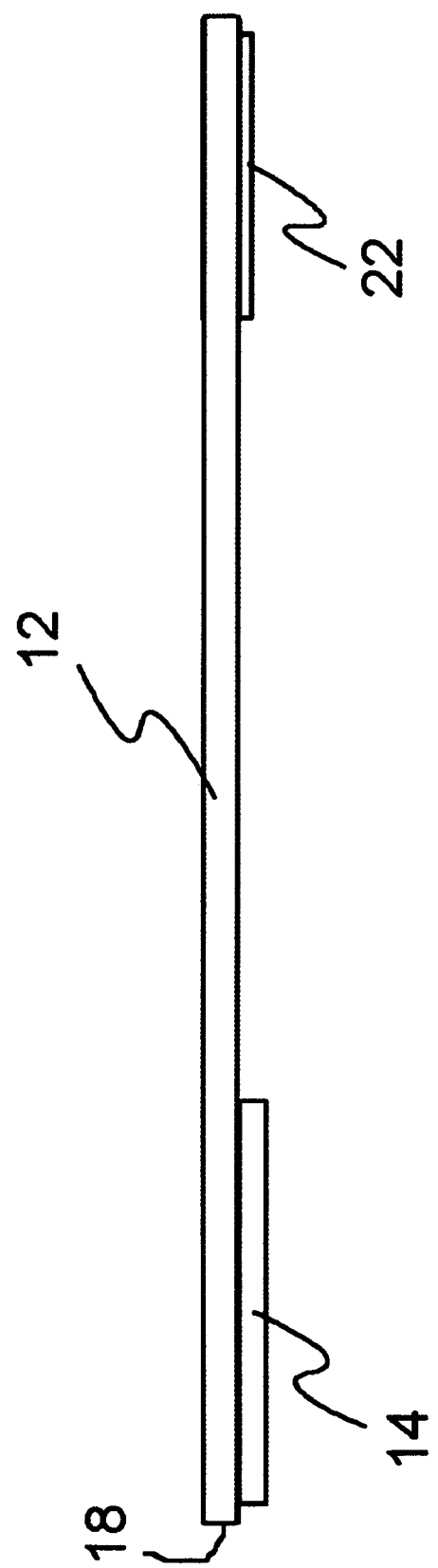
FIG. 2B is a side plane view of the self-adhering bandage depicted in FIG. 2.

Referring now to FIG. 2 and FIG. 2B, an alternative embodiment of the invention is depicted. The bandage (10) of FIG. 2 is a bandage where the width of dressing component (14) is shorter than the width of backing component (12). Such a configuration creates a border region (34) around the dressing component (14). Additionally, it should be appreciated that attachment mechanism (22) is associated with the first face of said backing component (12) at the second end (20) of backing component (12). As shown in FIG. 2, the width of attachment mechanism (22) may also be shorter than the width of backing component (12).

Figure 2C:
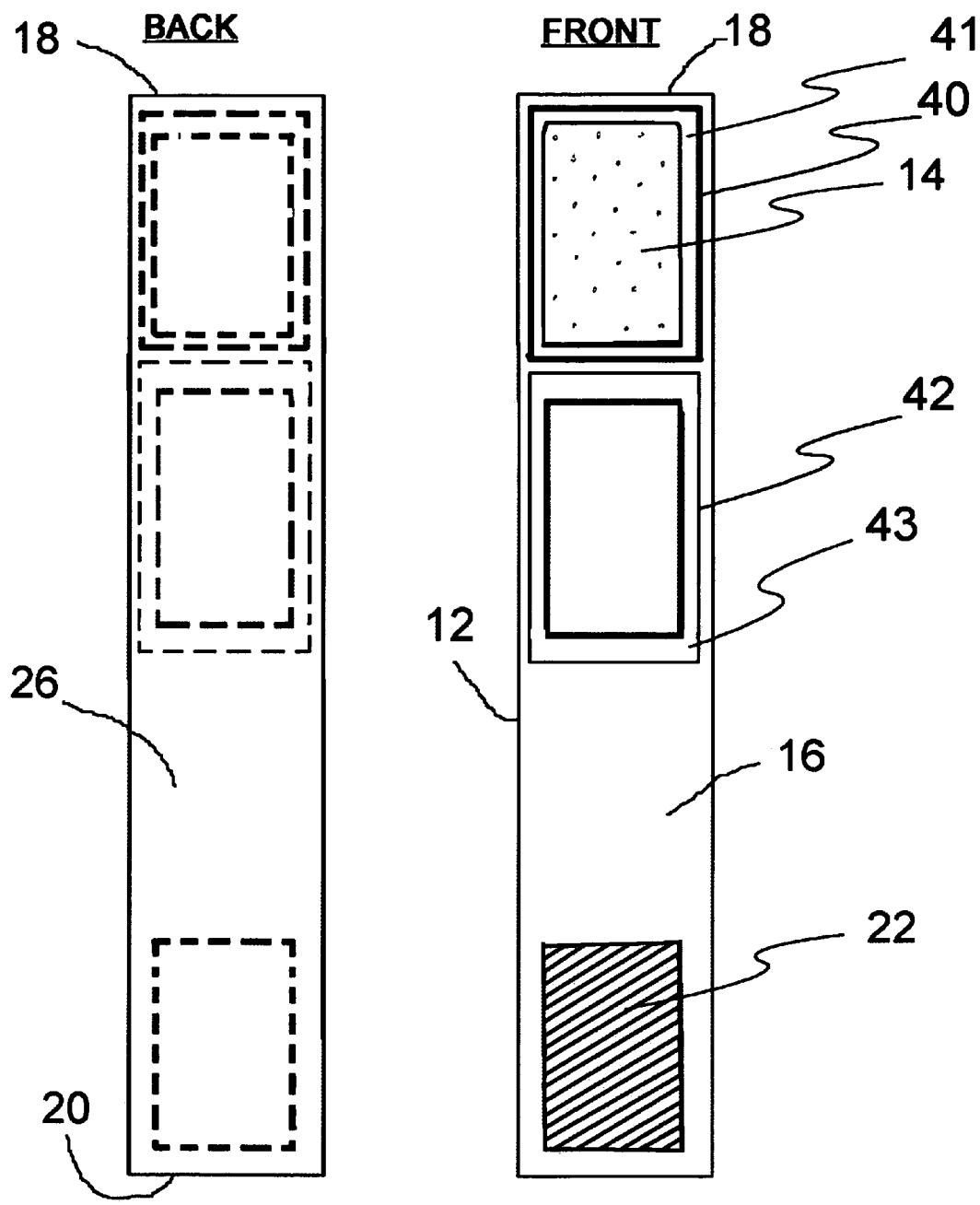
FIG. 2C is a back view and a front view of a self-adhering bandage according to another alternative embodiment of the present invention comprising two dressing component receivers disposed on a backing component and positioned adjacent to each other.
Figure 2D:
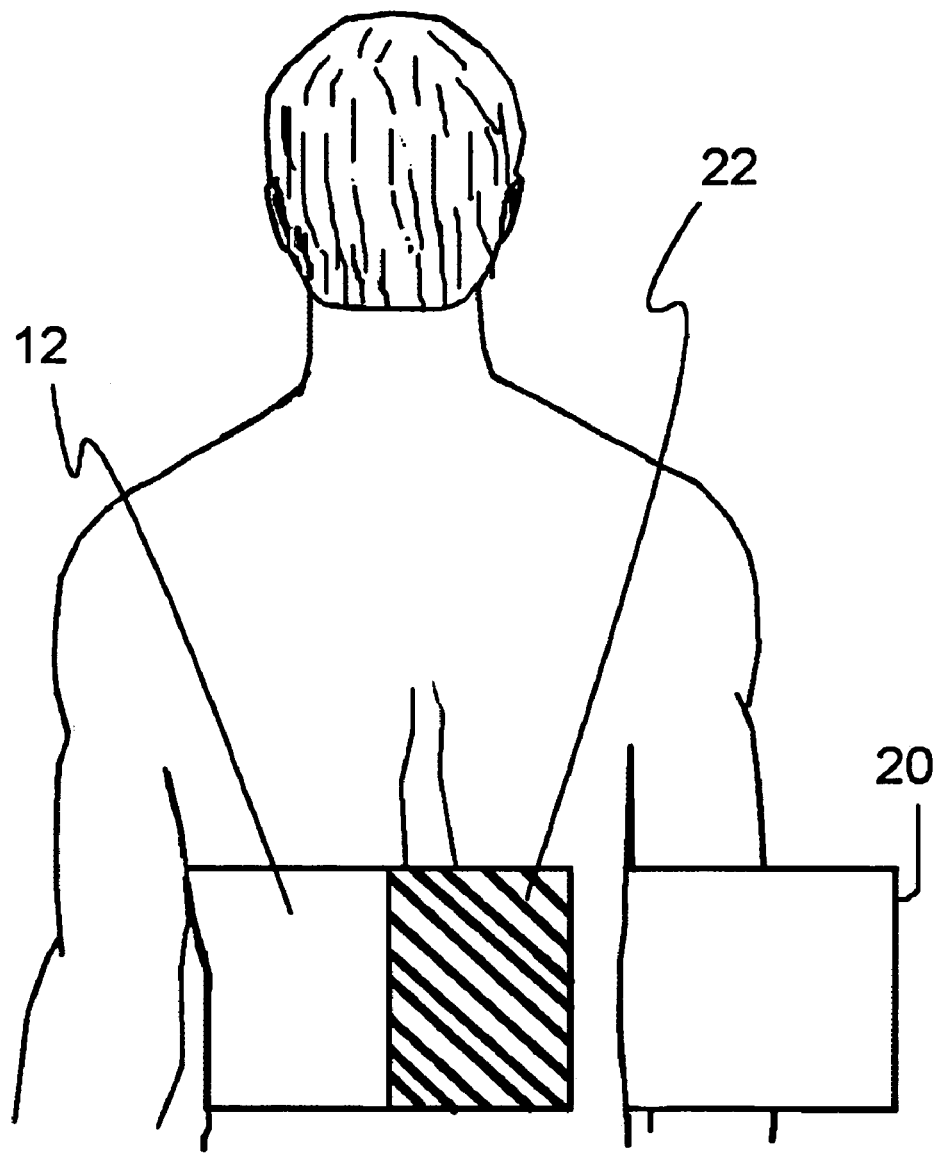
FIG. 2D is a view of a self-adhering bandage being applied to the back of a body.

As shown in FIG. 2D, bandages according to the present invention may be constructed large enough to cover huge sections of a body. It should be appreciated that while frequent dressing changes may be required, and while the type of dressing needed will likely change over the life of a particular wound, the general shape of the bandage needed is unlikely to change significantly between consecutive dressing changes. Consequently, to make the use of such a bandage more efficient, the FIG. 2C embodiment of the invention comprises dressing receiver (40) and (42). Dressing receiver (40) may be of any suitable technology for associating dressing (14) to backing component (12). For the embodiment shown in FIG. 2C, dressing receiver (40) and (42) comprise a generally rectangular frame attached to backing component (12). On the opposing side of dressing receiver (40) and (42) are dressing receiver interfaces (41, 43). The dressing receiver interfaces (41, 43) are suitably configured for releasably receiving a dressing. Similarly, a side of dressing component (14) may also comprise a dressing interface comprising material that will releasably attach to dressing receiver interface (41, 43). Alternatively, the dressing component (14) may be comprised of material that will releasably attach with dressing receiver interface (41, 43).

For such embodiments of the invention, attachment mechanism (22) preferably releasably attaches one face of the backing component (12) to the other face so that the same attachment mechanism (22) can be used repeatedly. As mentioned earlier, an attachment mechanism comprising hook and loop technology would be one possible embodiment.

As shown in FIG. 2C, any number of dressing receivers may be associated with backing component (12) without departing from the scope of the invention. It should be appreciated that with such a configuration, all components of the bandage except the dressing component may be reused. Any number of technologies may be used for associating dressing component (14) to backing component (12) and such technologies are well known and understood by those skilled in the art, and a detailed explanation thereof is not necessary for purposes of describing the method and system according to the present invention.

FIGS. 2E and 2F show an alternative embodiment of a dressing receiver interface (46) integral to backing component (12) and a dressing component interface (45) integral to dressing component (14).

Figure 3:
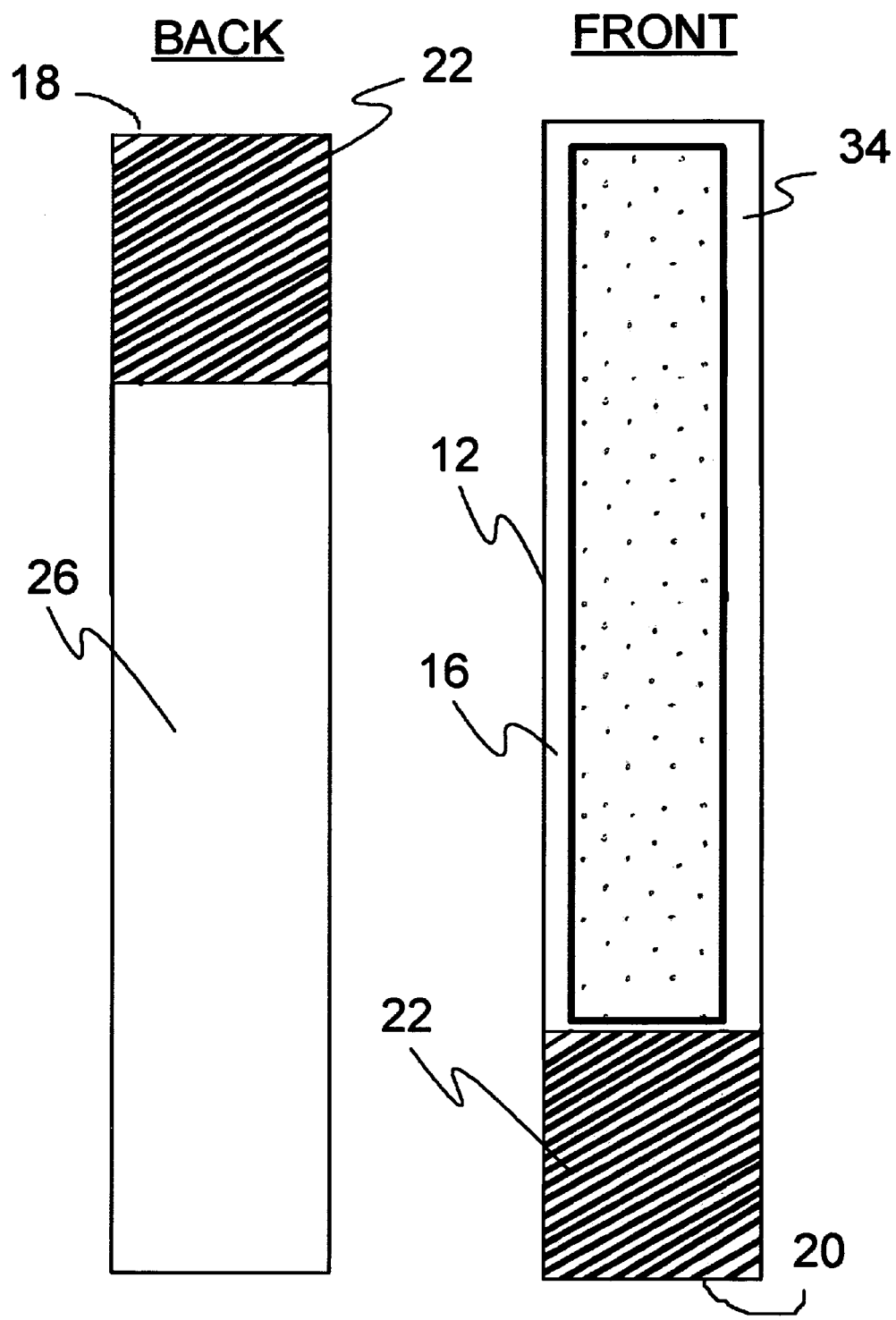
FIG. 3 is a back view and a front view of a self-adhering bandage according to another alternative embodiment of the present invention.
Figure 3B:
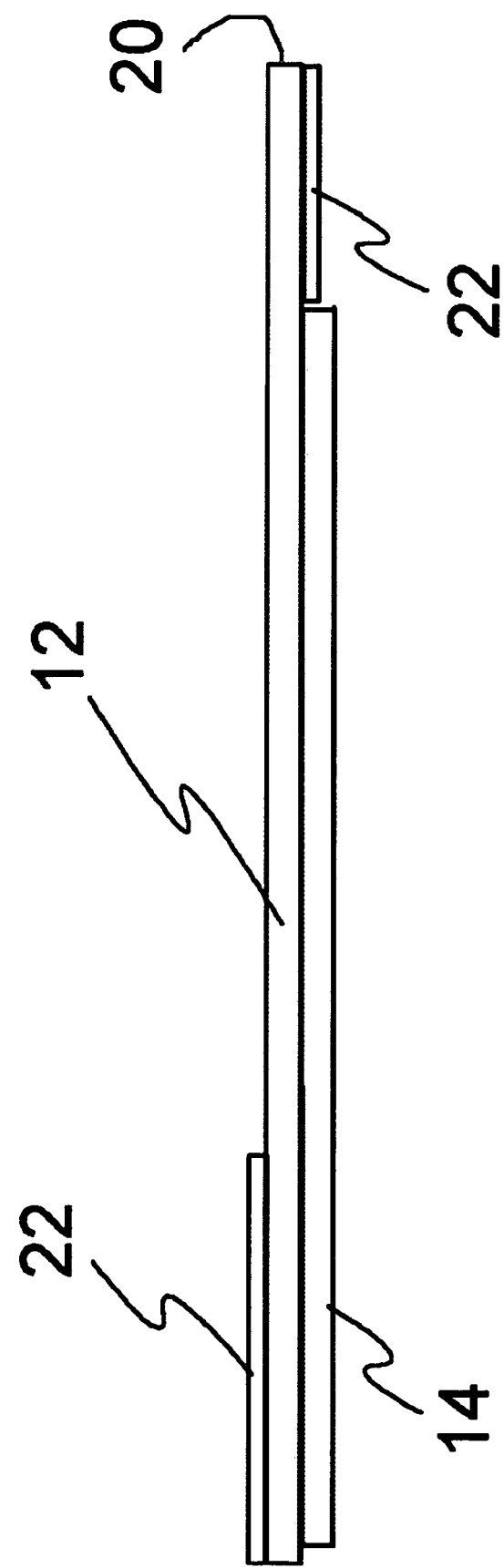
FIG. 3B is a side plane view of the self-adhering bandage depicted in FIG. 3.

Referring now to FIG. 3 and FIG. 3B, an alternative embodiment is depicted where the width of dressing component (14) is shorter than backing component's (12) b-width (30) but the width of attachment mechanism (22) is substantially equal to the width of backing component (12). Additionally, there is an attachment mechanism (22) disposed on first face (16) at second end (20) of the backing component (12). Similarly, an attachment mechanism (22) is disposed on second face (26) at the first end of backing component (12). Notably, the dressing component (14) runs along the first face (16) from about the start of first end (18) to the edge of attachment mechanism (22) near second end (20).

Figure 4:
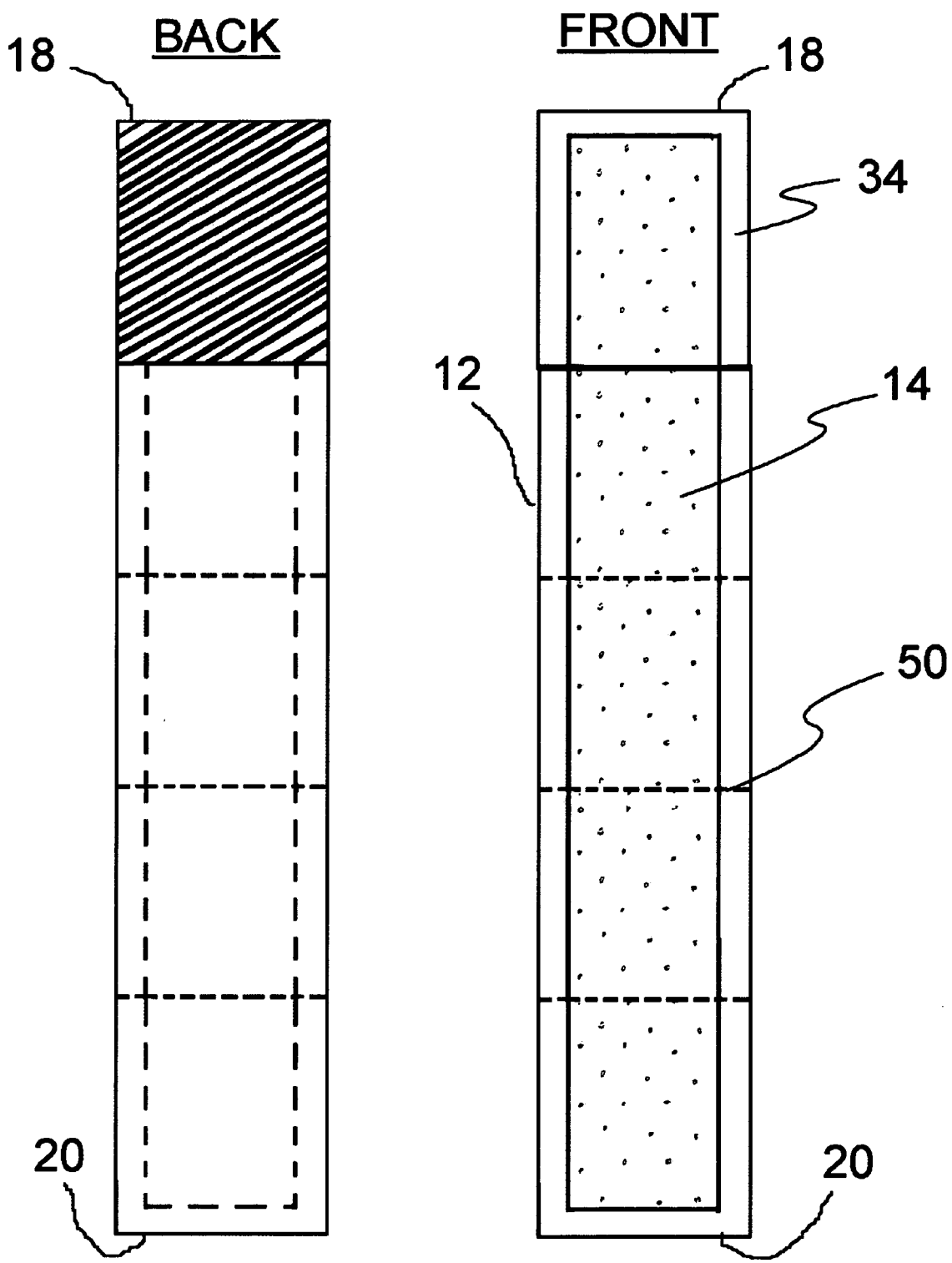
FIG. 4 is a back view and a front view of a self-adhering bandage according to another alternative embodiment of the present invention.
Figure 5A:
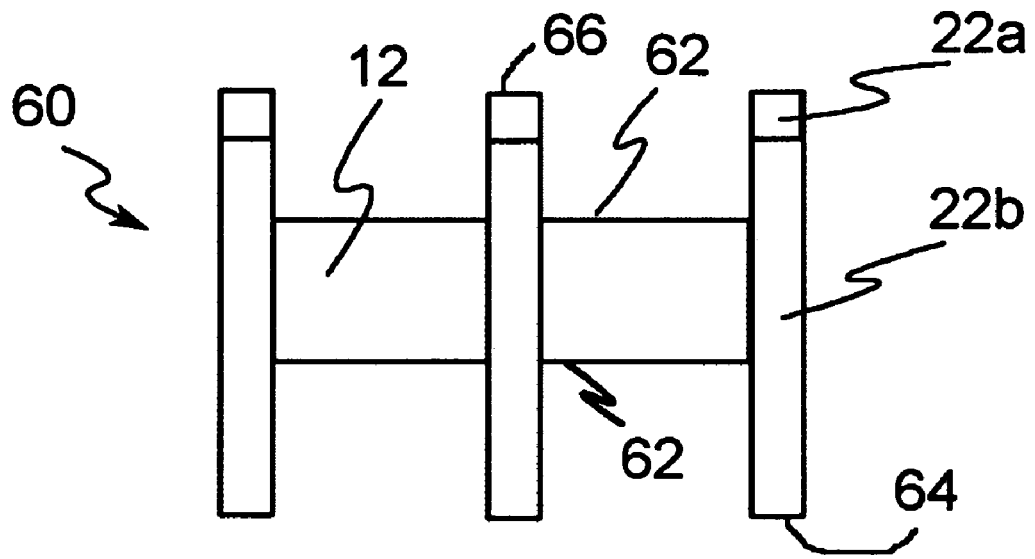
FIG. 5A is a back view of a self-adhering bandage according to another alternative embodiment of the present invention.
Figure 5B:
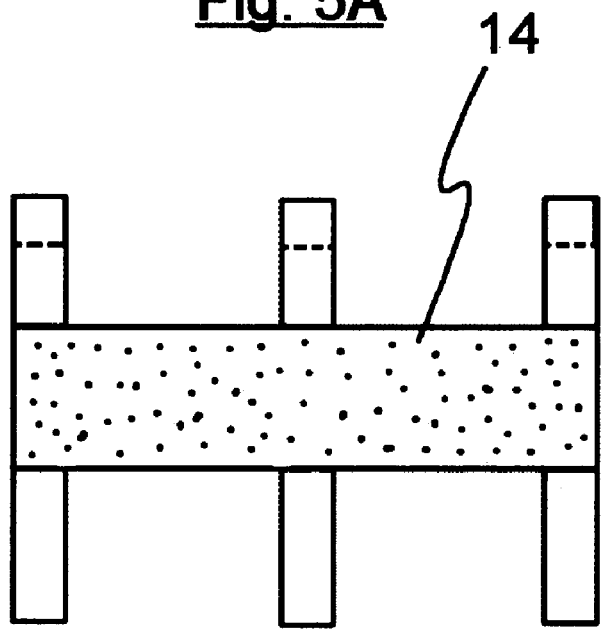
FIG. 5B is a front view of a self-adhering bandage according to another alternative embodiment of the present invention.
Figure 5D:
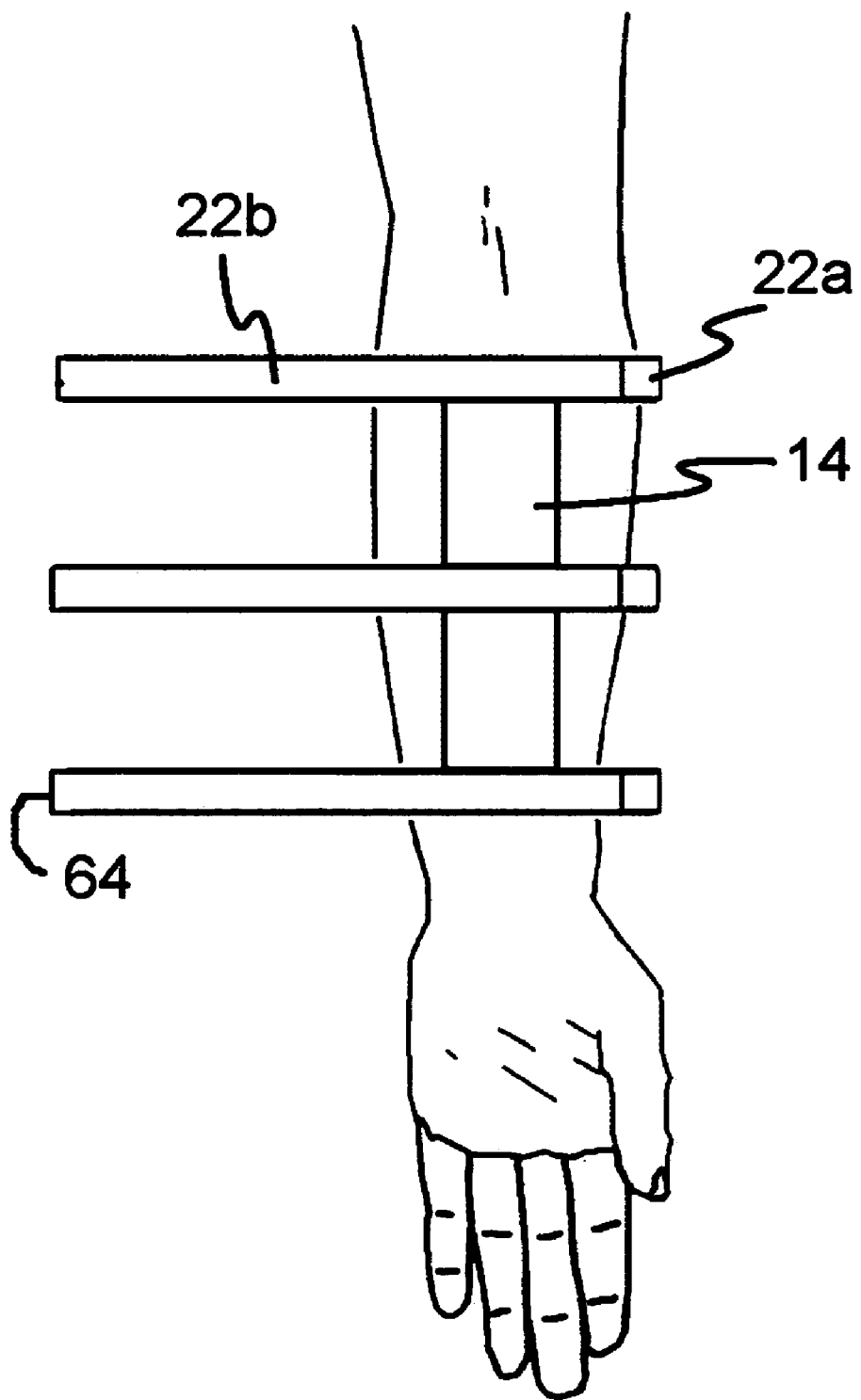
FIG. 5D is a top view of a self-adhering bandage being applied to an arm.

Referring now to FIG. 4 and FIG. 4B, another exemplary embodiment of the invention is depicted. For this embodiment, dressing component (14) runs along first face (16) from about the first end (18) of backing component (12) to about the edge of second end (20) of backing component (12). Horizontal Perforations (50) are included to allow easy removal of sections of bandage (10). It will be appreciated that for some embodiments such perforations may be run vertically along the bandage and for yet other configurations there may be both horizontal and vertical perforations. For yet another alternative embodiment depicted in FIG. 4C, the attachment mechanism (22) is associated with face (16) at second end (20).

Referring now to FIG. 5A, FIG. 5B, FIG. 5C, and FIG. 5D, yet another exemplary embodiment of the invention is depicted. For this exemplary embodiment, a plurality of attachment mechanisms attach to backing component (12) and extend perpendicularly outward from backing component (12). Each attachment mechanism comprises a strap section (22b) associated with an attachment section (22a) at one end of the strap section (22b). It should be appreciated that while backing component (12) is shown position about halfway between strap end (66) and strap end (64), the backing component (12) may be position at any point along strap section (22a) without departing from the scope of the present invention.

As shown in FIG. 5C, bandage (60) comprises an optional resilient component (62) that runs along the outer edge of backing component (14). Resilient component (62) creates a bow in bandage (60) when the bandage has not been applied to a wound, as indicated by angle (70) in FIG. 5C. When applied to a wound and secured by strap section (22a), the resilient component (62) tends to form a seal around the wound in the areas between the strap sections.

Figure 6A:
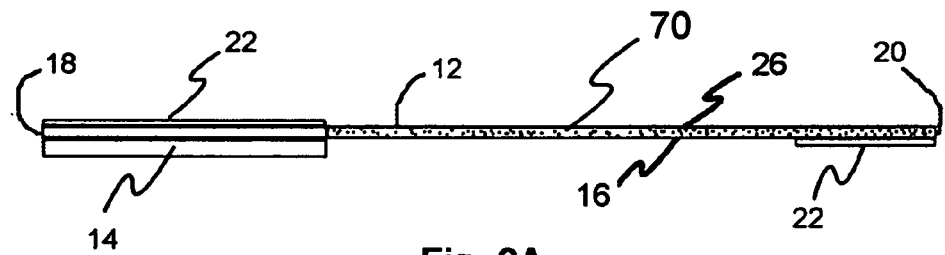
FIG. 6A is a side plane view of self-adhering bandage according to another alternative embodiment of the present invention comprising a void housing a substance.
Figure 6B:
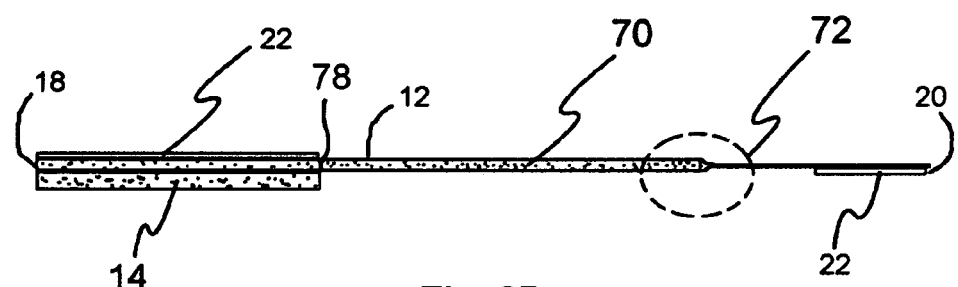
FIG. 6B is a side plane view of self-adhering bandage depicted in FIG. 6A showing the substance being transferred to the dressing component.
Figure 6C:
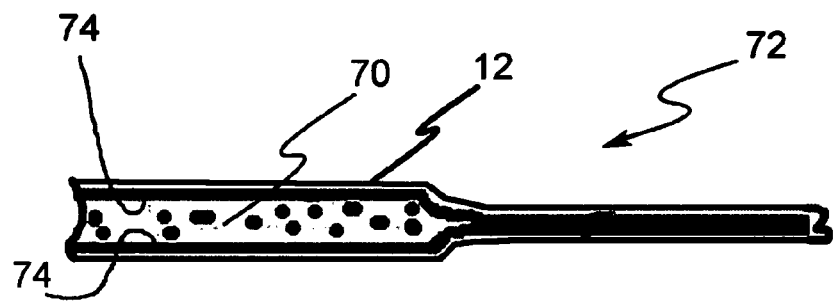
FIG. 6C is a side plane close up view of the bandage depicted in FIG. 6B.
Figure 7:
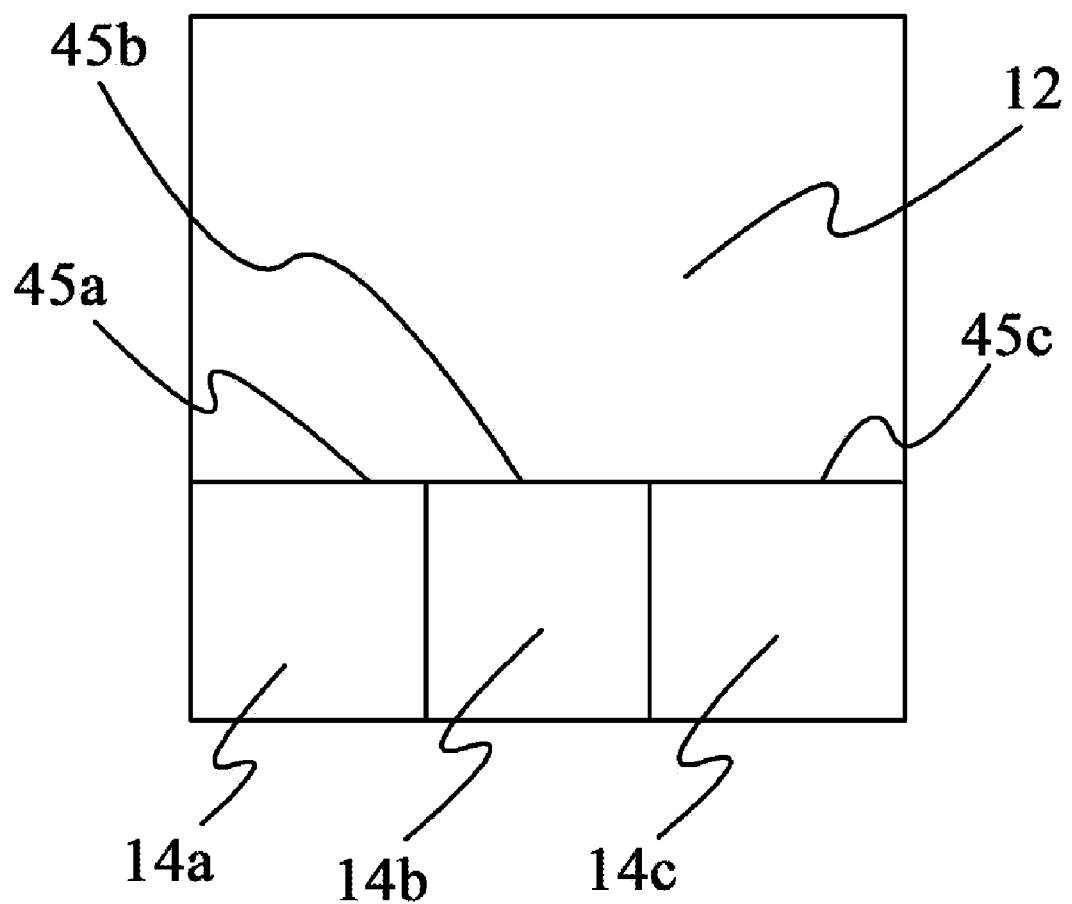
FIG. 7 is a top view of one alternative embodiment of the bandage depicted in FIG. 2E.

FIG. 6A, FIG. 6B, and FIG. 6C depicts another exemplary embodiment of the present invention. The bandage depicted in FIGS. 6A-6C is similar to the previously described bandages with the exception of a feature for housing a substance to be applied to dressing component (14). As noted previously, some wound dressing may be coated with medications or other substances to promote healing. In addition, some wounds may require a combination of substances to treat a wound where the two substances should not be combined before applying the combination to the wound. The bandage depicted in FIGS. 6A-6C address such issues.

For the embodiment depicted in FIG. 6A-C, the backing component (12) defines a void (70) between said first face (16) and said second face (26). Void (70) is configured for housing a substance to be applied to dressing component (14) when the dressing component is associated with a wound. For this embodiment, backing element (12) may be at least partially constructed of materials configured for holding the substance in void (70). Alternatively, backing element (12) may be lined with a material (74) that forms a bladder for holding the substance in void (70). The bladder formed by material (74) terminates at a passage (78). Passage (78) separates the remainder of the backing component (12) and the dressing component (14) from the substance housed in void (70). When pressure is applied to void (70), the bladder collapses as shown at (72) and at least part of the substance in void (70) is transferred to dressing component (14) and/or the remainder of backing component (12). The bladder formed by material (74) may be made of non-resilient material to prevent the substance from transferring back to void (70). Alternatively, passage (78) may be a one way passage.

While the present subject matter has been described in detail with respect to specific embodiments thereof, it will be appreciated that those skilled in the art, upon attaining an understanding of the foregoing may readily adapt the present technology for alterations to, variations of, and equivalents to such embodiments. Accordingly, the scope of the present disclosure is by way of example rather than by way of limitation, and the subject disclosure does not preclude inclusion of such modifications, variations, and/or additions to the present subject matter as would be readily apparent to one of ordinary skill in the art.

What is claimed is:

1. A bandage for covering a wound, comprising:
   a continuous backing component comprising a first backing face opposed by a second backing face wherein said first backing face and said second backing face define a backing component b-thickness, b-length, b-width, a backing component first end, and a backing component second end;

a dressing component comprising a first dressing component face opposed by a second dressing component face wherein the distance between said first dressing component face and said second dressing component face define a dressing component dc-thickness, said dressing component further defining a dressing component interface defining a dci-thickness that is less than said b-thickness;

wherein said backing component further defines a dressing receiver interface defining a dri-thickness substantially equal to said b-thickness minus said dci-thickness, said dressing receiver interface configured for associating with said dressing component interface so that said first dressing face and said first backing face define a substantially flat plane when the first backing face, second backing face, first dressing face, and said second dressing face are in horizontal alignment; and an attachment mechanism associated with at least one of (a) the first backing face at the first end of said backing component, and (b) the second backing face of said backing component.

2. A bandage for covering a wound as in claim 1, wherein the dc-thickness defined by the dressing component is substantially equal to the b-thickness defined by said backing component and wherein said dri-thickness is about equal to said b-thickness minus said dci-thickness so that said second dressing face and said second backing face define a substantially flat plane when the first backing face, second backing face, first dressing face, and said second dressing face are in horizontal alignment.

3. A bandage for covering a wound as in claim 2, comprising a plurality of dressing components, wherein a first dressing component associated with a first dressing receiver interface defines a passive section and a second dressing component associated with a second dressing receiver interface defines an interactive section.

4. A bandage for covering a wound as in claim 1, comprising a plurality of dressing components, wherein a first dressing component defines a passive section and a second dressing component defines a bioactive section.

5. A bandage for covering a wound as in claim 1, comprising a first dressing component associated with a first dressing receiver interface defining a interactive section and a second dressing component associated with a second dressing receiver interface defining a bioactive section.

6. A bandage for covering a wound as in claim 1, wherein said dressing component defines at least a first section and a different second section configured for treating wound areas in different stages of healing, wherein said first section comprises one of (a) a antimicrobial dressing, (b) a diabetic gel dressing, and (c) a cutinova dressing.

7. A bandage for covering a wound as in claim 1, wherein the dressing component comprises a patch constructed from materials in the fluoropolymers family and coated with a moisturizing layer.

8. A bandage for covering a wound as in claim 1, wherein the dressing component comprises a plurality of sections for covering one of (a) a wound having wound sections at different stages of healing and (b) two different wounds in close proximity to each other.

9. A bandage for covering a wound as in claim 8, wherein said dressing component comprises at least two sections selected from the group of sections consisting of:

(a) passive section;
(b) interactive section; and
(c) bioactive section.

10. A bandage for covering a wound as in claim 1, wherein the backing component defines a void between said first backing face and said second backing face, wherein a substance is disposed within said void, and wherein at least part of said substance is transferred to said dressing component when pressure is applied to the backing component defining said void.

11. A bandage for covering a wound as in claim 10, wherein said backing component defining said void is composed at least partially of a non-resilient material to inhibit said substance from transferring from the dressing component to the void and wherein said second dressing face and said second backing face define a substantially flat plane when said void is filled with said substance.

12. A bandage for covering a wound, comprising:
a backing component defining a first backing component portion and a second backing component portion, each backing component portion comprising a first face opposed by a second face, wherein the distance between said first face and said second face for each backing component portion defines a backing component portion b-thickness;

wherein only said first backing component portion defines a void between the first face of said first backing component portion and the second face of said first backing component portion;

a first dressing component associated with the first face of said second backing component portion and in fluid communication with said void;

wherein at least one substance is disposed within said void;

wherein said first backing component portion is made of a non-resilient material configured to non-resiliently collapse and transfer at least part of said substance to said first dressing component.

13. A bandage for covering a wound as in claim 12, wherein the parameter of said first dressing component is about equal to the parameter of said send void.

14. A bandage for covering a wound as in claim 12, further comprises a second dressing component associated with the first face of said first backing component portion and in fluid communication with said void.

15. A bandage for covering a wound as in claim 14, wherein said first dressing component defines a first bandage section that is different from a second bandage section defined by said second dressing component.

16. A bandage for covering a wound as in claim 12, wherein said first dressing component defines a first bandage section and said second dressing component defines a second bandage section and wherein said first bandage section is separated from said second bandage section by a transition region wherein said transition region is substantially the same size as the first bandage section.

17. A method of making a bandage for covering a wound, said method comprising the steps of:
providing a backing component defining an elongated bc-body disposed about a longitudinally extending axis, said bc-body defining a pair of opposed bc-faces, each of said bc-faces defining a first end and opposed second end, wherein each of said be face bc-faces defines a substantially flat plane that is substantially parallel to the other bc-face when the first end and second end of said opposed bc-faces are in horizontal alignment, wherein the peripheral edge of said opposed bc-faces define the parameter of the bc-body, wherein the distance between said opposed bc-faces defines a bc-thickness, wherein the width of said opposed bc-faces defines a bc-width, and wherein the length of said opposed bc-faces defines a bc-length;

providing a dressing component defining an elongated dc-body disposed about a longitudinally extending axis, said dc-body defining a pair of opposed dc-faces, wherein each dc-face defines a first end and opposed second end, each said dc-face defining a substantially flat plane wherein each said plane is substantially parallel to the other when the first end and second end of said opposed dc-faces are in horizontal alignment, wherein the peripheral edge of said opposed dc-faces define the parameter of the dc-body, and wherein the distance between said opposed dc-faces defines a dc-thickness, wherein the width of said opposed dc-faces defines a dc-width, and wherein the length of said opposed dc-faces defines a dc-length;

wherein said dressing component further defines a dressing component interface having a dci-thickness that is less than said bc-thickness and wherein at least one of said opposed bc-faces defines at least one dressing receiver interface having a dri-thickness that is substantially equal to said bc-thickness minus said dci-thickness;

associating said dressing component interface with said dressing receiver interface thereby defining a dressing-side dc-face; and providing an attachment mechanism configured for securing the bandage in place, said attachment mechanism associated with at least one of (a) the dressing-side dc-face at a location distal to the location of said dressing component, (b) the dc-face opposite to said dressing-side dc-face.

18. A method of making a bandage for covering a wound as in claim 17, further comprising the steps of:

providing a dressing component having a dc-thickness that is substantially equal to said bc-thickness and wherein said dri-thickness is about equal to said thickness bc-thickness minus said dci-thickness.

19. A method of making a bandage for covering a wound as in claim 18, further comprising the steps of:

configuring said opposed bc-faces to define a void there between thereby defining a bc-void portion, wherein said bc-void portion is in fluid communication with said dressing component;

providing a fluid flow path between said bc-void portion and said dressing component; and configuring said bc-void portion to non-resiliently collapse so that at least a portion of said substance is transferred from said bc-void portion to said first void dressing component when a pressure is applied to said bc-void portion.

* * * * *